US008034379B2

(12) United States Patent
Gorissen et al.

(10) Patent No.: US 8,034,379 B2
(45) Date of Patent: Oct. 11, 2011

(54) ION-STRENGTH INDEPENDENT SUSTAINED RELEASE PHARMACEUTICAL FORMULATION

(75) Inventors: Henricus R. M. Gorissen, Weesp (NL); Henderik W. Frijlink, Weesp (NL)

(73) Assignee: Solvay Pharmaceuticals B.V., Weesp (NL)

( * ) Notice: Subject to any disclaimer, the term of this patent is extended or adjusted under 35 U.S.C. 154(b) by 1213 days.

(21) Appl. No.: 10/381,714

(22) PCT Filed: Sep. 28, 2001

(86) PCT No.: PCT/EP01/11285
§ 371 (c)(1),
(2), (4) Date: Mar. 28, 2003

(87) PCT Pub. No.: WO02/26214
PCT Pub. Date: Apr. 4, 2002

(65) Prior Publication Data
US 2004/0013727 A1 Jan. 22, 2004

(30) Foreign Application Priority Data

Sep. 29, 2000 (EP) .................................. 00203381
Sep. 29, 2000 (NL) .................................. 1016295

(51) Int. Cl.
*A61K 9/20* (2006.01)
*A61K 9/28* (2006.01)
*A61K 9/14* (2006.01)
(52) U.S. Cl. ..................... 424/464; 424/474; 424/484
(58) Field of Classification Search .............. 424/464, 424/465, 468, 474, 484
See application file for complete search history.

(56) References Cited

U.S. PATENT DOCUMENTS

| 4,389,393 A | | 6/1983 | Schor et al. ............. 424/19 |
| 4,871,548 A | | 10/1989 | Edgren et al. ............ 424/488 |
| 5,324,732 A | * | 6/1994 | Schoen et al. ............ 514/278 |
| 5,387,419 A | * | 2/1995 | Levy et al. ............. 424/422 |
| 2002/0150622 A1 | | 10/2002 | Philbrook et al. ......... 424/486 |

FOREIGN PATENT DOCUMENTS

| EP | 0 923 934 A1 | | 6/1999 |
| FR | 2 588 188 | | 4/1987 |
| WO | WO 96/14070 | | 5/1996 |
| WO | WO 98/47491 | | 10/1998 |
| WO | WO 99/47125 | | 9/1999 |
| WO | WO 00/19985 | * | 4/2000 |
| WO | WO 00/21525 | | 4/2000 |

OTHER PUBLICATIONS

Pillay, V. et al., Electrolyte-Induced Compositional Heterogeneity: A Novel Approach for Rate-Controlled Oral Drug Delivery, Journal of Pharmaceutical Sciences, vol. 88, No. 11, pp. 1140-1148, Nov. 1999.
International Search Report for PCT/EP01/11285.

* cited by examiner

*Primary Examiner* — Yong Chong
(74) *Attorney, Agent, or Firm* — Finnegan, Henderson, Farabow, Garrett & Dunner, L.L.P.

(57) ABSTRACT

The present invention is related to an optionally coated pharmaceutical hydrophilic gel forming matrix formulation comprising one or more active substances and having a prolonged release of said one or more active substances upon exposure to gastrointestinal fluids, characterized in that said release is substantially ion-strength independent. The invention is further related to a method of preparing this formulation which can be used in the administration of active substances for the treatment of a large number of disorders.

34 Claims, No Drawings

ION-STRENGTH INDEPENDENT SUSTAINED RELEASE PHARMACEUTICAL FORMULATION

This application is a National Stage application under 35 U.S.C. §371 of PCT/EP/01/11285, filed Sep. 28, 2001, which claims priority from applications EP 00203381.9, filed Sep. 29, 2000, and NL 1016295, filed Sep. 29, 2000.

The present invention is related to a pharmaceutical formulation with a substantially sustained release behavior which is independent of the ion-strength of the dissolution medium, e.g. the gastrointestinal fluid. The sustained release is achieved over a time period up to 16 hours. The dosage form combines one or more active substances with a mixture of hydrophilic polymer carriers resulting in a gel forming matrix formulation.

Hydrophilic gel forming matrix formulations are well know dosage forms to control the dissolution behavior of active substances. The mechanism by which the active substance is released, starts with the hydration of the dosage form surface to form a gel structure. Simultaneously the active substance at the formulation surface dissolves in the dissolution medium. In the stationary phase, the dissolution medium continuously penetrates the gel structure and the gel expands. The active substance dissolves in the dissolution medium and is transported to the outer layer of the gel. Meanwhile, erosion of the outer layers of the gel occurs. Finally the release levels off, caused by the decreased concentration gradient of the active substance in the formulation and the penetrated dissolution medium. This mechanism is described in the prior art, e.g. Manford Robinson. The Theory and Practice of Industrial Pharmacy, $2^{nd}$ edition, Chapter 14: "Sustained Action Dosage Forms".

Hydrophilic polymers used in the above described formulations are mostly polysaccharide carriers such as the cellulose derivates hydroxypropylmethylcellulose (HPMC), hydroxypropylcellulose (HPC), hydroxyethylcellulose (HEC), sodium carboxymethylcellulose (NaCMC) or combinations of these cellulose derivatives.

Formulations of these type are described in numerous patents and patent applications, e.g. in U.S. Pat. No. 4,871,548 and EP-A-0923934.

U.S. Pat. No. 4,871,548 discloses a controlled release dosage form comprising an active compound and a mixture of at least a low viscosity cellulose ether and a high viscosity cellulose ether. EP-A-0923934 discloses a modified release matrix formulation of cefaclor and cephalexin comprising 5-35% of a mixture of hydrophilic polymers of different grades, wherein the hydrophilic polymers comprise about 0.1% to about 20% by weight of medium viscosity hydroxypropyl methylcellulose and about 0.1% to about 20% of low viscosity hydroxypropylcellulose Although the above mentioned formulations are described as sustained release formulations in general, this sustained release only appears when the concentration of salts, the ion-strength, in the dissolution medium is low. The release rate of the active substance from the above mentioned formulation may be substantially dependent on the ion-strength. A high ion-strength may even lead to so-called dose-dumping. In this case the total amount of active substance is released in a very short time, which may lead to undesired, and even dangerous high blood levels of the active substance. A high ion-strength often occurs direct after taking a meal. As patients often take their medication just after a meal there is a high risk that ion-strength dependent formulations give rise to unwanted fast release of active substance instead of the desired sustained release.

WO 98/47491 describes a sustained release formulation wherein the control of the release of the active substance is based on a combination of two so called 'intelligent' polymers, having opposing wettability characteristics, one demonstrating a stronger tendency towards hydrophobicity and the other a stronger tendency towards hydrophilicity. In this formulation dose dumping can only be prevented by coating with an enteric coating.

It is the objective of the present invention to provide a sustained release formulation which is substantially independent from the ion-strength of the dissolution medium, which is normally the gastrointestinal fluid even when the formulation is not coated. It is obvious for a person skilled in the art that the formulation should also meet the normal physical and pharmaceutical requirements in the art, such as good flowing properties of the powder during tabletting, a crushing strength of compressed tablets of at least 30 N, a friability below 1% at a compression force between 10 and 40 KN, uniformity of content and sufficient stability. Further it is a requirement that the formulation can be prepared using normal formulation procedures and equipment, so that no large investments are necessary.

This objective can be achieved, according to the present invention, by a pharmaceutical hydrophilic gel forming matrix formulation having a prolonged release of one or more active substances upon exposure to gastrointestinal fluids, characterized in that said release is substantially ion-strength independent.

Prolonged release is defined as a (gradual) release of the active substance from the dosage form over a time period of 45 minutes or more. This period starts usually with the administration of the dosage form, or with the start of in-vitro dissolution test (the moment the dosage form is brought into the dissolution medium).

By the term substantially ion-strength independent is meant that the release rate profile of the active substance is not significantly changed (according to General Chapter 711: Physical tests and Determinations in USP 24 (±10% of label claim)) when the ion strength (I) is varied between 0.05 and 0.45 mol/l. The ion strength (I) is defined as $I=\frac{1}{2}\Sigma c z_i^2$, in which c is the concentration of the different ions in the solution and $z_i$ their respective charge number (Handbook of Chemistry and Physics $71^{st}$ edition, David R. Lide ed., page 2-18, Boston, CRC Press Inc.; 1990-1991).

Although a coating is not essential to achieve the independency of the ion-strength, the formulation is optionally coated with a coating material in order to achieve another desired effect, such as masking of the taste or application of color. Suitable coating materials are known in the art and are for example HPMC, acrylics, ethylcellulose (see Graham Cole ed., Pharmaceutical Coating Technology, London, Taylor & Francis Ltd.; 1995)

The hydrophilic gel forming matrix has the form of tablets or of a multi-particulate dosage form and preferably contains a mixture of at lease two hydrophilic high viscosity cellulose ethers. Although the presence of a hydrophobic cellulose ether such as ethylcellulose will normally have no detrimental effect on the release properties of the present formulation, preferably no substantial amount of said hydrophobic cellulose ether is present. With a substantial amount of hydrophobic cellulose ether is meant an amount greater than 20% of the total weight of the gel forming polymers.

Cellulose ethers are well known in the art and are available in pharmaceutical grades and with different average molecular weights leading to different viscosities of a solution of these cellulose ethers. For the purpose of this patent application, hydrophilic polymers may be characterized by their viscosities in a 2% w/w aqueous solution as low viscosity (less than about 1000 mPas), medium viscosity (about 1000 mPas to about 10,000 mPas) and high viscosity (greater than about 10,000 mPas)

Hydrophilic hydroxypropyl methylcellulose polymers (HPMC's) which may be used in the present invention are available in different viscosity grades from Dow Chemical Co. under the brand name Methocel® and from Shin Etsu under the brand name Metolose®.

Examples of low viscosity polymers are Methocel E5®, Methodcel E-15LV®, Methocel E50LV®, Methocel K100LV® and Methocel F50LV®, whose 2% aqueous solutions at 25° C. have viscosities of 5 mPas, 15 mPas, 50 mPas, 100 mPas and 50 mPas, respectively.

Examples of medium viscosity HPMC's are Methocel E4M® and Methocel K4M, whose 2% aqueous solutions at 25° C. have viscosities of 4000 mPas.

Examples of high viscosity HPMC's are Methocel K15M® and Methocel K100M® whose 2% aqueous solutions at 25° C. have viscosities of 15,000 mPas and 100,000 mPas.

Hydrophilic hydroxyethylcellulose polymers (HEC's) which may be used in the present invention are available in different viscosity grades from AQUALON under the brand name Natrosol® and from Amerchol Corporation under the brand name Cellosize®.

Examples of low viscosity polymers are Natrosol L® en Natrosol J®, whose 2% aqueous solutions at 25° C. have viscosities of 10 mPas and 20 mPas, respectively.

Examples of medium viscosity polymers are Natrosol G® and Natrosol K® whose 2% aqueous solutions at 25° C. have viscosities of 200 mPas and 1500 mPas, respectively.

Examples of high viscosity polymers are Natrosol M® and Natrosol HH® whose 2% aqueous solutions have viscosities at 25° C. of 4000 mPas and 90000 mPas, respectively.

In a preferred embodiment of the present invention the formulation comprises a mixture of a high or medium viscosity hydroxypropylmethylcellulose (HPMC) and a high or medium viscosity hydroxyethylcellulose (HEC). The ratio between the high or medium viscosity HPMC and the high or medium viscosity HEC is 1/0.85 to 1/1.2, preferably is 1/0.9 to 1/1.1, even more preferably is 1/0.95 to 1/1.05 and most preferred is 1/1. The formulation optionally may comprise a low viscosity HPMC. In that case the ratio between high or medium viscosity HPMC and low viscosity HPMC is in the range between 1/0.01 and 1/0.2 and preferably is between 110.01 and 1/0.1 and even more preferably is between 1/0.02 and 1/0.05.

It has surprisingly been found that formulations having the above mentioned composition can be used to prepare tablets that have a release rate that is independent of the ion-strength in the range that is normal in the gastro-intestinal fluid. Said normal range is between 0.17 and 0.35 mol/L.

Apart from its independence from the ion-strength, the release controlling principle of the formulation is also substantially independent from the pH in the range between pH=1.3 and pH=7.4. This means that the release rate of active substance is not influenced by the pH in those cases where the active substance release is not limited by the solubility of the active substance, i.e. that the differences in release values (in %) at a given point in time are less than 20% of the label claim (see Chapter Dissolution Specifications (page 1080-81) in FIP Guidelines for Dissolution Testing of Solid Oral Products (Final Draft, 1995), Drug Information Journal 1996, Vol 30, 1071-84) within the whole pH range between 1.3 and 7.4.

Because of its optimal properties as a sustained release formulation, the formulation according to the present invention can be used in the treatment of a large series of diseases in the case that sustained release properties are desirable. Examples of active substances that can be formulated into a sustained release formulation are active substances for the treatment of CNS disorders, including schizophrenia, episodic paroxysmal anxiety (EPA) disorders such as obsessive compulsive disorder (OCD), post traumatic stress disorder (PTSD), phobia and panic, major depressive disorder, bipolar disorder, Parkinson's disease, general anxiety disorder, autism, delirium, multiple sclerosis, Alzheimer disease/dementia and other neurodegenerative diseases, severe mental retardation and dyskinesias, such as Huntington's disease or Gilles dela Tourett's syndrome, anorexia, bulimia, stroke, addiction/dependency/craving, sleep disorder, epilepsy, migraine; attention deficit/hyperactivity disorder (ADHD); cardiovascular diseases including heart failure, angina pectoris, arrhythmias, myocardial infarction, cardiac hypertrophy, hypotension, hypertension—e.g. essential hypertension, renal hypertension, or pulmonary hypertension, thrombosis, arteriosclerosis, cerebral vasospasm, subarachnoid hemorrhage, cerebral ischemia, cerebral infarction, peripheral vascular disease, Raynaud's disease, kidney disease—e.g. renal failure; dyslipidemias; obesity; emesis; gastrointestinal disorders including irritable bowel syndrome (IBS), inflammatory bowel disease (IBD), gastroesophagal reflux disease (GERD), motility disorders and conditions of delayed gastric emptying, such as postoperative or diabetic gastroparesis, and diabetes, ulcers—e.g. gastric ulcer; diarrhoea; other diseases including osteoporosis; gynecological disorders, inflammations; infections such as bacterial, fungal, protozoan and viral infections, particularly infections caused by HIV-1 or HIV-2; pain; cancers; chemotherapy induced injury; tumor invasion; immune disorders; urinary retention; asthma; allergies; arthritis; benign prostatic hypertrophy; endotoxin shock; sepsis; complication of diabetes mellitus.

Preferred active substances to be formulated are active substances that are used for the treatment of CNS disorders, such as fluvoxamine (5-methoxy-1-[4-(trifluoro-methyl)phenyl]-1-pentanone O-(2-aminoethyl)oxime) or flesinoxan ((+)-benzamide, N-[2-[4-[(2R)-2,3-dihydro-2-(hydroxymethyl)-1,4-benzodioxin-5-yl]-1-piperazinyl]ethyl]-4-fluoro), for the treatment of cardiovascular disorders, such as tedisamil (N,N'-dicyclopropylmethyl-9,9-tetramethylene-3,7-diazabicyclo[3.3.1]-nonane) or propanolol or active substances that are used in the treatment of gynecological disorders e.g. in Hormone Replacement Therapy, such as dydrogesterone, estradiol or conjugated estrogens. The present invention is especially useful for the formulation of the active substance flesinoxan, especially as its monohydrochloride ((+)-benzamide, N-[2-[4-[(2R)-2,3-dihydro-2-(hydroxymethyl)-1,4-benzodioxin-5-yl]-1-piperazinyl]ethyl]-4-fluoro-monohydrochloride), described in EP0138280 and EP307061 and for tedisamil, preferably as its sequifumarate (N,N'-dicyclopropylmethyl-9,9-tetramethylene-3,7-diazabicyclo-[3.3.1]-nonane 1.5 hydrogenfumarate), described in EP 0550383.

The present invention also relates to a method of preparing a formulation as described above, characterized in that (1) a core is compressed of a mixture comprising one or more active substances and a mixture of at least two hydrophilic high or medium viscosity cellulose ethers yielding a substantially ion-strength independent and prolonged substantially zero-order release of active substances; and (2) the core is optionally coated.

The ingredients HPMC, HEC, active substance, pigment blend and glidant are mixed in a suitable mixer. This powder mixture is blended with sodium stearyl fumarate in a suitable mixer.

The active substance may be added in the form of a pregranulate to the powder mixture used to compress. Alternatively the powder mixture for tabletting may be produced by a mixing procedure that is followed by a (wet or dry) granulation process.

The mixture of ingredients is compressed into tablets with commercial available equipment (e.g. a Courtoy® R0) using flow regulating agents like colloidal silica and lubricating agents like talcum, sodium stearyl fumarate or magnesium stearate. The quantity of hydrophilic celluloses in the complete formulation ranges between 15% and 99.5%, while the amount of active substance ranges between 0.1% and 80%. The amount of flow regulating and lubricating agent is fixed to improve powder flow properties and to prevent sticking of powder to the dye walls or the punches. The amount of glidant is between 0.05% and 5% and is preferably about 0.2%. The amount of lubricant is between 0.05% and 5% and is preferably about 0.4%. For commercial reasons, the powder mixture may be coloured with between 0.1% and 10% pigment blend. Typical pigment blends are commercially available, e.g. from COLORCON® as Opadry.®

All publications, including but not limited to patents and patent applications, cited in this specification are herein incorporated by reference as if each individual publication were specifically and individually indicated to be incorporated by reference herein as though fully set forth.

The following examples are only intended to further illustrate the invention, in more detail, and therefore these example are not deemed to restrict the scope of the invention in any way.

EXAMPLE 1

Preparation of an Ion-Strength Independent Formulation

EXAMPLE 1a

General Procedure for the Preparation

First colloidal silica is passed through a sieve. Said sieve possesses preferably a screen between 0.40 mm and 0.595 mm. The active substance is mixed together with the hydrophilic celluloses, colloidal silica, pigment blend and if required mannitol in a suitable mixer. Said mixer is preferably a high shear mixer with the granulator in off position. The sodium stearyl fumarate is passed through a sieve. Said sieve possesses preferably a screen between 0.40 mm and 0.595 mm. The powder mixture is compressed into tablets with the desired dimensions. The compression equipment is preferably a rotary machine, like Korsch and Courtoy equipment. Optional, the tablets can be coated with water soluble celluloses or derivates of cellulose like ethylcellulose or acrylates based on aqueous suspensions or organic solvents. The coating process is preferably carried out in perforated drum equipment or with equipment based on fluidized bed technology.

TABLE 1

The composition of non-coated tablets (cores), expressed in mg/tablet.

| Materials | Flesinoxan Label claim: 2 mg/t | Acetaminophen Label claim 2.2 mg/t | Fluvoxamine maleate Label claim: 100 mg/t | Tedisamil. di HCl Label claim: 100 mg/t | Tedisamil sesqui fumarate Label claim: 150 mg/t |
|---|---|---|---|---|---|
| Flesinoxan•HCl | 2.18 | n.a. | n.a. | n.a. | n.a. |
| Acetaminophene | n.a. | 2.19 | n.a. | n.a. | n.a. |
| Fluvoxamine maleate | n.a. | n.a. | 100.00 | n.a. | n.a. |
| Tedisamil.diHCl | n.a. | n.a. | n.a. | 124.4 | n.a. |
| Tedisamil.sesqui fum. | n.a. | n.a. | n.a. | n.a. | 240.0 |
| HPMC K4M | 69.63 | 69.63 | 17.00 | 125.2 | 81.0 |
| HPMC E5 | 7.50 | 7.50 | 12.50 | 20.0 | 14.0 |
| HEC HX250PH | 69.63 | 69.63 | 17.00 | 125.2 | 81.0 |
| Mannitol SD200 | n.a. | n.a. | 100.00 | n.a. | n.a. |
| Colloidal silica | 0.30 | 0.30 | 0.50 | 1.60 | 4.0 |
| Pigment blend PB23015 | 0.15 | 0.15 | n.a. | 0.40 | n.a. |
| Sodium stearyl fumarate | 0.60 | 0.60 | 3.00 | 3.20 | 5.0 |
| Total tablet weight (mg) | 150.00 | 150.00 | 250.00 | 400.00 | 425.00 | n.a.: not applicable

TABLE 2

Properties of several compositions

| Tablet property | Flesinoxan Label claim: 2 mg/t | Acetaminophen Label claim 2.2 mg/t | Fluvoxamine maleat Label claim: 100 mg/t Coated | Tedisamil. diHCl Label claim: 100 mg/t | Tedisamil s squi fumarate Label claim: 150 mg/t |
|---|---|---|---|---|---|
| Tablet dimension (mm) | 5.5 × 11.0 mm Special shaped | 7.0 mm round | 8.0 mm round | 8.0 × 15.0 mm oblong | 8.0 × 15.0 mm oblong |
| Tablet weight (mg) | 150 | 150 | 275 | 400 | 425 |

TABLE 2-continued

Properties of several compositions

| Tablet property | Flesinoxan Label claim: 2 mg/t | Acetaminophen Label claim 2.2 mg/t | Fluvoxamine maleat Label claim: 100 mg/t Coated | Tedisamil. diHCl Label claim: 100 mg/t | Tedisamil s squi fumarate Label claim: 150 mg/t |
|---|---|---|---|---|---|
| Crushing strength (N) | 83 | 75 | 144 | 71 | 90 |
| Friability (%) | not determined | not determined | not determined | 0.4 | 0.05 |
| Release profile | Table 4 | Table 4 | Table 4 | Table 4 | Table 4 |

EXAMPLE 1b

Release Properties of Several Formulations

The release of the active substance from the hydrophilic matrix tablets is measured in the USP apparatus If using paddles rotating at 50 rpm in either an USP dissolution buffer medium pH 6.8 of 0.05 molar (M), 0.17 M and 0.34 M prepared from di sodium hydrogen phosphate.2aq and citric acid.1aq (coded as F, G and H respectively) or in a half-change dissolution medium prepared from 0.1 M aqueous hydro chloride solution in the first part of the test (90 minutes) followed by 0.2 M pH 6.8 by adjusting with tri sodium phosphate.12 aq in the second part of the test. To increase the ionic strength of the aqueous solution during the test, sodium chloride is added to the solution. 1 liter dissolution medium of part two contains an amount of sodium chloride of respectively 0 gram (dissolution medium A), 10 gram (dissolution medium B), 15 gram (dissolution medium C), 30 gram (dissolution medium D1 and D2), and 50 gram (dissolution medium E1 and E2). In the dissolution media B, C, D1 and E1 the sodium chloride is only added in the second part of the test. In the dissolution media D2 and E2 75% of the sodium chloride is added in the first part of the test and 25% in the second part. The release of the active substance is measured over 16 hours with sample intervals of one hour during the first two hours followed by sample intervals of two hours over the remaining test period. Samples may be analysed on-line with a HPLC system or by UV spectroscopy. The release of the different active compounds from the formulation is given in the tables 4a-4c.

From the release data as given in the tables 4a-4c is can be concluded that the release of active substance from the formulation according to the present invention is substantially independent from the pH and the ion-strength, as differences in release values are less than 20%. Further it can be concluded that there is no substantial difference between the release profile when the ion-strength is increased at low pH (pH 1.2) and at higher pH (pH 6.8)

TABLE 3

Overview of dissolution media

| Dissolution method | | Dissolution medium | | | | | |
|---|---|---|---|---|---|---|---|
| | | A | B | C | D1 | D2 | E1 | E2 |
| 1) pH 1.2 | 1.5 hours | 750 ml 0.1 HCl | | | | | | |
| | NaCl added (g) | | | | | 22.5 | | 37.5 |
| 2) pH 6.8 | 14.5 hours | 250 ml 0.2 M Na$_3$PO$_4$•12 aq | | | | | | |
| | NaCl added (g) | 0 | 10 | 15 | 30 | 7.5 | 50 | 12.5 |
| Ion Strength (mol/L) in final dissolution medium | | 0.14 | 0.31 | 0.40 | 0.65 | 0.65 | 1.00 | 1.00 |

| Dissolution method | | Dissolution medium | | |
|---|---|---|---|---|
| | | F | G | H |
| pH 6.8 | Na$_2$HPO$_4$•2 aq + citric acid•1 aq | 0.05 M | 0.17 M | 0.34 M |
| Ion Strength (mol/L) | | 0.11 | 0.38 | 0.77 |

TABLE 4a

Release of several non-coated tablet compositions as function of time

| Amount of active sutstance (%) Released after | Flesinoxan Label claim: 2 mg/t | | | | Acetaminophen Label claim 2.2 mg/t | | | Fluvoxamine maleate Label claim: 100 mg/t | | |
|---|---|---|---|---|---|---|---|---|---|---|
| Dissolution medium | A | B | D1 | E1 | F | G | H | A | B | C |
| 0 hours | 0 | 0 | 0 | 0 | 0 | 0 | 0 | 0 | 0 | 0 |
| 1 hour | 20 | 18 | 20 | 18 | 21 | 15 | 25 | 22 | 22 | 22 |
| 2 hours | 32 | 28 | 31 | 30 | 34 | 29 | 38 | 36 | 36 | 35 |
| 6 hours | 59 | 52 | 53 | 50 | 70 | 63 | 70 | 67 | 66 | 64 |
| 16 hours | 91 | 84 | 83 | 79 | 107 | 105 | 103 | 99 | 99 | 99 |

TABLE 4b

Release f several non-coated tablet compositions as function of time

| Amount of active substance (%) Released after | Tedisamil.di HCl Label claim: 100 mg/t | | | Tedisamil sesqul fumarate Label claim 150 mg/t | | | | |
|---|---|---|---|---|---|---|---|---|
| Dissolution medium | A | B | C | A | D1 | D2 | E1 | E2 |
| 0 hours | 0 | 0 | 0 | 2 | 0 | 0 | 2 | 0 |
| 1 hour | 32 | 32 | 33 | 20 | 18 | 20 | 20 | 21 |
| 2 hours | 50 | 51 | 52 | 32 | 24 | 32 | 32 | 33 |
| 6 hours | 84 | 85 | 84 | 47 | 45 | 49 | 47 | 52 |
| 16 hours | 92 | 94 | 93 | 79 | 75 | 76 | 75 | 81 |

TABLE 4c

Release of tedisamil sesqui fumarate non-coated tablet in one single dissolution medium as function of time

| Amount of active substance (%) | Tedisamil.sesqui fumarate Label claim: 150 mg/t | |
|---|---|---|
| Released after Dissolution medium | 750 ml 0.1 M HCl (pH 1.2) | 750 ml 0.1 M HCl + 250 ml 0.2 M Na$_3$PO$_4$•12 aq (pH 6.8) |
| 0 hours | 0 | 0 |
| 1 hour | 20 | 13 |
| 2 hours | 33 | 22 |
| 6 hours | 64 | 48 |
| 16 hours | 97 | 89 |

The invention claimed is:

1. A pharmaceutical formulation comprising:
   a hydrophilic gel forming matrix comprising at least one hydroxypropylmethylcellulose polymer chosen from high and medium viscosity polymers, and at least one hydroxyethylcellulose polymer chosen from high and medium viscosity polymers, wherein the at least one hydroxypropylmethylcellulose polymer and the at least one hydroxyethylcellulose polymer are present in a ratio ranging from about 1:0.85 to about 1:1.2; and
   at least one pharmaceutically active substance;
   wherein said pharmaceutically active substance is released from said formulation in a substantially ion-strength independent manner by the hydrophilic gel forming matrix.

2. The pharmaceutical formulation according to claim 1, wherein said formulation is coated.

3. The pharmaceutical formulation according to claim 1, wherein said ratio ranges from about 1:0.9 to about 1:1.1.

4. The pharmaceutical formulation according to claim 3, wherein said ratio ranges from about 1:0.95 to about 1:1.05.

5. The pharmaceutical formulation according to claim 4, wherein said ratio is about 1:1.

6. The pharmaceutical formulation according to claim 1, wherein said at least one hydroxypropylmethylcellulose polymer and said at least one hydroxyethylcellulose polymer are chosen from high viscosity polymers.

7. The pharmaceutical formulation according to claim 1, wherein said at least one hydroxypropylmethylcellulose polymer comprises a medium viscosity polymer and wherein said at least one hydroxyethylcellulose polymer comprises a high viscosity polymer.

8. The pharmaceutical formulation according to claim 1, wherein said at least one hydroxypropylmethylcellulose polymer comprises a high viscosity polymer and wherein said at least one hydroxyethylcellulose polymer comprises a medium viscosity polymer.

9. The pharmaceutical formulation according to claim 1, wherein said at least one hydroxypropylmethylcellulose polymer and said at least one hydroxyethylcellulose polymer are chosen from medium viscosity polymers.

10. The pharmaceutical formulation according to claim 1, further comprising at least one low viscosity hydroxypropylmethylcellulose polymer.

11. The pharmaceutical formulation according to claim 10, wherein said at least one high and/or medium viscosity hydroxypropylmethylcellulose polymer and said at least one low viscosity hydroxypropylmethylcellulose polymer are present in a ratio ranging from about 1:0.01 to about 1:0.2.

12. The pharmaceutical formulation according to claim 1, wherein said formulation comprises less than about 20 w/w % of an ethylcellulose polymer, relative to the total weight of all cellulose polymers.

13. The pharmaceutical formulation according to claim 1, wherein said at least one pharmaceutically active substance is chosen from substances for the treatment of at least one condition chosen from CNS disorders, cardiovascular diseases, dyslipidemias, obesity, emesis, gastrointestinal disorders, diarrhoea, gynecological disorders, osteoporosis, inflammations, bacterial infections, fungal infections, protozoan infections, viral infections, pain, cancers, chemotherapy-induced injury, tumor invasion, immune disorders, urinary retention, asthma, allergies, arthritis, benign prostatic hypertrophy, endotoxin shock, sepsis, and complications of diabetes mellitus.

14. A pharmaceutical formulation according to claim 13, wherein said CNS disorders are chosen from schizophrenia, episodic paroxysmal anxiety disorders, major depressive disorder, bipolar disorder, Parkinson's disease, general anxiety disorder, autism, delirium, multiple sclerosis, neurodegenerative diseases, severe mental retardation, dyskinesias, anorexia, bulimia, stroke, addiction, dependency, craving, sleep disorder, epilepsy, migraine, and attention deficit/hyperactivity disorder.

15. A pharmaceutical formulation according to claim 14, wherein said episodic paroxysmal anxiety disorders are chosen from obsessive compulsive disorder, post traumatic stress disorder, phobia, and panic.

16. A pharmaceutical formulation according to claim 14, wherein said neurodegenerative diseases are chosen from Alzheimer's disease and dementia.

17. A pharmaceutical formulation according to claim 14, wherein said dyskinesias are chosen from Huntington's disease and Gilles dela Tourett's syndrome.

18. The pharmaceutical formulation according to claim 13, wherein said cardiovascular diseases are chosen from heart failure, angina pectoris, arrhythmias, myocardial infarction, cardiac hypertrophy, hypotension, hypertension, thrombosis, arteriosclerosis, cerebral vasospasm, subarachnoid hemorrhage, cerebral ischemia, cerebral infarction, peripheral vascular disease, Raynaud's disease, and kidney disease.

19. A pharmaceutical formulation according to claim 18, wherein said hypertension is chosen from essential hypertension, renal hypertension, and pulmonary hypertension.

20. A pharmaceutical formulation according to claim 13, wherein said gastrointestinal disorders are chosen from irritable bowel syndrome, inflammatory bowel disease, gastroesophagal reflux disease, motility disorders, and conditions of delayed gastric emptying.

21. A pharmaceutical formulation according to claim 20, wherein said conditions of delayed gastric emptying are chosen from postoperative gastroparesis, diabetic gastroparesis, and gastric ulcer.

22. A pharmaceutical formulation according to claim 13, wherein said viral infections are chosen from infections caused by HIV-1 and HIV-2.

23. The pharmaceutical formulation according to claim 1, wherein said at least one pharmaceutically active substance is chosen from fluvoxamine, flesinoxan, tedisamil, propranolol, pharmaceutically acceptable salts of any of the foregoing, and substances used in hormone replacement therapy.

24. A pharmaceutical formulation according to claim 23, wherein said substances used in hormone replacement therapy are chosen from dydrogesterone, estradiol, and conjugated estrogens.

25. A pharmaceutical formulation according to claim 23, wherein said at least one pharmaceutically active substance is chosen from fluvoxamine, flesinoxan, and pharmaceutically acceptable salts of either of the foregoing.

26. A pharmaceutical formulation according to claim 25, wherein said at least one pharmaceutically active substance comprises flesinoxan monohydrochloride.

27. The pharmaceutical formulation according to claim 23, wherein said at least one pharmaceutically active substance is chosen from tedisamil, propranolol, and pharmaceutically acceptable salts thereof.

28. The pharmaceutical formulation according to claim 27, wherein said at least one pharmaceutically active substance comprises tedisamil sesquifumarate.

29. The pharmaceutical formulation according to claim 1 that is in the form of a tablet.

30. The pharmaceutical formulation according to claim 29, further comprising a coating substantially covering said tablet.

31. The pharmaceutical formulation according to claim 1, wherein said at least one pharmaceutically active substance is released from the formulation in a pH-independent manner when the pH ranges from about 1.3 to about 7.4.

32. A method of preparing a pharmaceutical formulation comprising mixing at least one pharmaceutically active substance and a hydrophilic gel forming matrix comprising at least one hydroxypropylmethylcellulose polymer chosen from high and medium viscosity polymers, and at least one hydroxyethylcellulose polymer chosen from high and medium viscosity polymers, wherein the at least one hydroxypropylmethylcellulose polymer and the at least one hydroxyethylcellulose polymer are present in a ratio ranging from about 1:0.85 to about 1:1.2, wherein said pharmaceutically active substance is released from said formulation in a substantially ion-strength independent manner by the hydrophilic gel forming matrix.

33. The method according to claim 32, further comprising compressing said mixture into a core.

34. The method according to claim 33, further comprising applying a coating to said core.

* * * * *